US006210570B1

(12) United States Patent
Holloway

(10) Patent No.: US 6,210,570 B1
(45) Date of Patent: *Apr. 3, 2001

(54) MONOLITHIC SILICA COLUMN

(75) Inventor: Robert R. Holloway, Montara, CA (US)

(73) Assignee: Agilent Technologies, Inc., Palo Alto, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/137,607

(22) Filed: Aug. 21, 1998

(51) Int. Cl.$^7$ .................................................. B01D 15/08
(52) U.S. Cl. ................................. 210/198.2; 210/502.1; 210/656; 96/101; 501/39
(58) Field of Search ........................ 210/198.2, 635, 210/656, 502.1; 501/12, 39; 96/101

(56) References Cited

U.S. PATENT DOCUMENTS

| Re. 34,457 | 11/1993 | Okamoto et al. | 210/198.2 |
|---|---|---|---|
| 3,808,125 | * 4/1974 | Good | 210/198.2 |
| 3,878,092 | * 4/1975 | Fuller | 210/198.2 |
| 4,112,032 | 9/1978 | Blaszyk et al. | 264/42 |
| 4,724,207 | 2/1988 | Hou et al. | 435/180 |
| 4,997,804 | 3/1991 | Pekala | 502/218 |
| 5,009,688 | 4/1991 | Nakanishi | 65/183 |
| 5,100,841 | 3/1992 | Wada et al. | 501/39 |
| 5,194,279 | 3/1993 | Okel | 426/330 |
| 5,307,438 | 4/1994 | Bilkadi et al. | 385/141 |
| 5,308,495 | * 5/1994 | Avnir | 210/198.2 |
| 5,334,310 | * 8/1994 | Frechet | 210/198.2 |
| 5,378,790 | 1/1995 | Michalczyk et al. | 528/35 |
| 5,522,994 | * 6/1996 | Frechet | 210/198.2 |
| 5,624,875 | 4/1997 | Nakanishi et al. | 501/39 |
| 5,628,907 | * 5/1997 | Hester | 210/659 |
| 5,637,135 | 6/1997 | Ottenstein et al. | 96/101 |
| 5,656,250 | 8/1997 | Tanaka et al. | 435/335 |
| 5,728,457 | * 3/1998 | Frechet | 210/198.2 |
| 5,750,610 | 5/1998 | Burns et al. | 524/434 |
| 5,772,875 | * 6/1998 | Petterson | 210/198.2 |

FOREIGN PATENT DOCUMENTS 0 363 697 A1   4/1990  (EP) ................................. 210/198.2

OTHER PUBLICATIONS

Acker, E.G., "The Characterization of Acid–Set Silica Hydrosols, Hydrogels, and Dried Gel," Journal of Colloid and Interface Science, vol. 32, No. 1, pp. 41–54, Jan. 1970.
Nakanishi, K. and Soga, N., "Phase Separation in Gelling Silica–Organic Polymer Solution: Systems Containing Poly(sodium styrenesulfonate)," J.Am.Ceram.Soc., vol. 74, No. 10, pp. 2518–2530, 1991.
Jones, W.M. and Fischbach, D.B., "Novel Processing of Silica Hydrosols and Gels," Journal of Non–Crystalline Solids 101, pp. 123–126, 1988.

(List continued on next page.)

*Primary Examiner*—Ernest G. Therkorn

(57) ABSTRACT

The present invention relates to capillary columns including a monolith and a method for preparing a capillary column including a monolith. The monolith can be prepared by a sol gel method, and in the transformation from hydrosol to hydrogel, the monolith undergoes essentially no syneresis or volume shrinkage. Thus, deleterious effects of syneresis are avoided, such as the formation of channels having large dimensions that provide a pathway of least resistance for a mobile phase to effectively bypass portions of a stationary phase. The method for preparing a column having a monolith that undergoes essentially no syneresis involves a hydrogel solution that has a relatively low concentration of $SiO_2$, i.e. less than about 5 g/100 mL.

5 Claims, 3 Drawing Sheets

OTHER PUBLICATIONS

Svec, F. and Frechet, J.M.J., "Continuous Rods of Macroporous Polymer as High–Performance Liquid Chromatography Separation Media," Anal. Chem. vol. 64, No. 7, pp. 820–822, Apr. 1, 1992.

Minakuchi, H., et al., "Octadecylsilylated Porous Silica Rods as Separation Media for Reversed–Phase Liquid Chromatography," Anal. Chem., vol. 68, No. 19, pp. 3498–3501, Oct. 1, 1996.

Brinker, C.J. and Scherer, G.W., "Sol–Gel Science The Physics and Chemistry of Sol–Gel Processing," Academic Press, NY. Chapter 6, Section 3, pp. 373–384, 1990.

Wendelken, S.C., "Development of a Sol–Gel Stationary Phase for Electrochromatography," UMI Dissertation Services, dissertation submitted to the Division of Graduate Studies and Research of the University of Cincinnati, 1996, pp. 1–181.

* cited by examiner

MONOLITHIC SILICA COLUMN

FIELD OF THE INVENTION

The present invention relates to a method for producing chromatography columns, in particular a silica column, via a sol-gel method. The initial hydrosol has a composition featuring less than 5% $SiO_2$ to produce a hydrogel that undergoes essentially no syneresis. The present invention also encompasses a capillary chromatography column including a novel monolith.

BACKGROUND OF THE INVENTION

There exists a variety of methods to separate a mixture of components by chromatographic methods, the methods generally involving the flow of a mobile phase over a stationary phase. For example in liquid chromatography, the mobile phase is a liquid and typically the stationary phase is a solid. The components to be separated are located within the mobile phase and can either be liquids or solutions, the solutions comprising liquids and/or solids dissolved in a solvent. The stationary phase has the properties of an adsorbent upon which the components of the mobile phase can be adsorbed. In the chromatographic process, as the mobile phase flows along the stationary phase, the components continually adsorb and desorb onto the stationary phase at a rate specific for a particular component. Rate differences between the various components allow for their separation.

In conventional liquid chromatography, the stationary phase can comprise a packed column of particles where efficient packing of the particles is essential in allowing optimum separation of components. Preferably, the stationary phase has a high surface area afforded by the surface area of the particles. If the particles are porous, an inner surface area can also exist as defined by pore dimensions to increase the overall surface area. A continued challenge in the field of chromatography is to improve resolution of component separation. Poor resolution is shown where bands of different components overlap excessively and the resulting chromatographed solutions retain a mixture of components. For example, poorly packed columns can generate large gaps or channels by which the mobile phase can effectively bypass portions of the stationary phase, resulting in poor resolution. In contrast, relatively little overlap between the bands of components defines good resolution. A combination of pore dimension, particle size and uniformity of particle packing contribute to affect the resolution of component separation.

In certain instances, however, an extremely well-packed column having particles of a small diameter and/or pore dimension can reduce the flow rate of the mobile phase due to a restricted mobile phase pathway. Consequently, higher pressures are required to provide an acceptable chromatographic flow rate. And at any given pressure, longer elution times result as the particle size and/or pore dimensions decrease.

To overcome the problems inherent in packed-particle columns, stationary phases comprising a continuous network have been developed. This continuous network phase or monolith can comprise pores of an appreciable dimension and at the same time, eliminate gaps or channels that can arise from poorly packed columns. For example, U.S. Pat. No. 5,624,875 relates to methods for preparing inorganic porous materials having pores of various desired dimensions.

There remain challenges to design chromatography columns and in particular, capillary columns that provide optimum resolution without requiring the longer operation times and/or increased pressure conditions. Prior art capillary columns typically involve a stationary phase permanently positioned within a circular cross-section tube having inner diameters ranging from 5 μm to 0.5 mm. The stationary phase comprises particles which are applied to an inner wall of the capillary at high pressures of up to a conventional maximum of 400 bar. Higher application pressures may be necessary depending on the length of a column. Example applications for such columns include capillary electrophoresis or high performance liquid chromatography.

SUMMARY OF THE INVENTION

The invention provides capillary column incorporating a monolith, and also a method for making the chromatography column.

One aspect of the invention provides a method for preparing a chromatography column. The method includes the step of providing an aqueous mixture including a compound having at least one hydrolyzable oxygen-containing group. The method also involves causing the mixture to form a hydrosol via a reaction involving the at least one hydrolyzable oxygen-containing group. The hydrosol is introduced into a capillary, the hydrosol having a first volume. Gellation of the hydrosol is induced to produce a monolith. The monolith has a second volume, wherein the second volume is at least about 95% of the first volume.

One embodiment of the invention provides a method for preparing a chromatography column. The method involves an aqueous mixture of a compound having at least one hydrolyzable oxygen-containing group formed into a hydrosol via a reaction involving the at least one hydrolyzable oxygen-containing group, the hydrosol being positioned in a capillary. The improvement comprises the hydrosol being selected to have a first volume, the hydrosol being induced to gel to produce a monolith. The monolith has a second volume, wherein the second volume is at least about 95%,o of the first volume.

Another aspect of the invention provides a capillary column. The column has a porous monolith, the monolith having pores of a first mean diameter and channels of a second mean diameter. The second mean diameter is greater than the first mean diameter by less than about 150% of the first mean diameter.

One embodiment provides a capillary column including a monolith wherein the column is free of deleterious effects due to syneresis.

Other advantages, novel features, and objects of the invention will become apparent from the following detailed description of the invention when considered in conjunction with the accompanying drawings, which are schematic and which are not intended to be drawn to scale. In the figures, each identical or nearly identical component that is illustrated in various figures is represented by a single numeral. For purposes of clarity, not every component is labeled in every figure, nor is every component of each embodiment of the invention shown where illustration is not necessary to allow those of ordinary skill in the art to understand the invention.

DETAILED DESCRIPTION

Figure 1A:
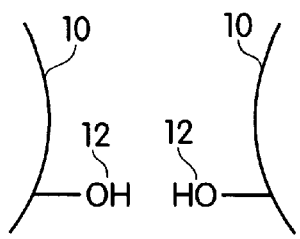
FIG. 1A is a schematic illustration of two surfaces each having a hydrolyzable hydroxide group.

The present invention relates to chromatography columns and reactants and reactant concentrations for preparing stationary phase materials that undergo essentially no syneresis. In particular, the stationary phase of the column comprises a continuous network, such as a monolith.

One aspect of the present invention provides a method for preparing a chromatography column. In one embodiment, chromatography columns can have stationary phases that are polar and these columns can comprise an inorganic oxide, such as alumina ($Al_2O_3$) or silica ($SiO_2$). Inorganic oxides can be formed by condensation reactions between compounds having condensible groups. One type of condensation reaction is hydrolysis, where reactions between hydrolyzable oxygen-containing groups, such as a hydroxide or an alkoxide, can produce an oxygen-bridge. In one embodiment, a silica stationary phase is formed, the method involving a hydrosilylation reaction between a silicon-containing compound having at least one hydrolyzable oxygen-containing group.

In another embodiment of the invention, the silicon-containing compound having at least one hydrolyzable oxygen-containing group is an alkoxysilane. Alkoxysilanes can have a formula $(R')_{4-x}Si(OR)_x$ where x is at least 1. To prepare an extended silica network having at least one dimension comprising a main Si—O—Si-containing chain, x is preferably at least two. To prepare an extended silica network having at least two main chains arising from the same silicon atom, x is preferably at least 3. R can be a hydrocarbon selected from the group consisting of $C_1$–$C_{12}$ alkyl, alkaryl and aryl. In another embodiment, the alkoxysilane has a formula $Si(OR)_4$ and R can be selected from the group consisting of methyl, ethyl, propyl and butyl. In another embodiment, the alkoxysilane is selected from the group consisting of tetramethylorthosilicate and tetraethylorthosilicate.

Another embodiment of the invention includes the step of forming a hydrosol from the alkoxysilane. A "sol gel" method involves the preparation of solid state materials from a solution containing soluble reactants. When a chemical reaction occurs, the products of the reaction may initially be soluble in the solution. Further reaction causes the products to increase in size until the products are no longer soluble and precipitate out of solution. At this point, the hydrosol is achieved, the "hydrosol" being a dispersion of discrete, amorphous particles, e.g. silica, of colloidal dimensions. The hydrosol can be caused to react even further to continually form larger particles until the hydrogel is formed. A "hydrogel" is a solid phase of the sol gel process comprising a continuous network of chemical bonds having boundaries defined by the container of the reaction. Those of ordinary skill in the art understand that the transformation from hydrosol to hydrogel is a continuous process due to the gradual increase in size of the particles to eventually form an interconnected network. Thus, a hydrogel is understood to be a solid integrated mass filling the entire container and a completely interconnected chemical bond pathway may not be easily proven. An advantage of the sol gel method is the control of reactants and reactant conditions, e.g. temperature, pH, concentrations, to ultimately affect the composition and structure of the final gel product.

In one embodiment, a hydrosol is formed by subjecting monomers, for example alkoxysilanes, to condensation or hydrolysis conditions. For example, in a reaction between two SiOR units where R can be a hydrocarbon, a product containing an RSi—O—SiR unit can result under hydrolyzable conditions. Other hydrolysis reactions can also occur, such as reaction between SiOR and $H_2O$ to produce SiOH groups. The hydrosol can then be induced to gellation conditions, resulting in formation of the "polymer" or hydrogel.

The hydrosol is typically formed under hydrolysis conditions which can involve the addition of a catalyst to a solution containing the alkoxysilane monomers. The solution can be an aqueous solution. The solution can also include any organic solvent, for example an alcohol preferably having less than six carbon atoms, such as methanol or ethanol. Hydrosol formation is generally dependent on a pH of the solution. Thus, at one pH level, a certain concentration or amount of reactants may be optimal for hydrosol formation whereas at another pH, the concentration or amount of reactants may differ. The pH can be controlled by the addition of acids or bases. In addition, the acids or bases can function as the catalyst, which can be selected from the group consisting of inorganic acids, inorganic bases, organic acids and organic bases. In another embodiment, the acids can be selected from the group consisting of nitric acid, hydrochloric acid, sulfuric acid and acetic acid. The hydrosol can be prepared at a temperature of preferably between about 0° C. and about 25° C. In one embodiment, the hydrosol can be prepared at cooler temperatures of between about 0° C. and about 10° C. to effectively separate the hydrosol formation stage from the hydrogel formation process by slowing down the hydrosol to hydrogel transformation.

Chromatography columns preferably comprise a high surface area, stationary phase material. Because separation of components is achieved by differentiating adsorption/desorption rates of the components as they traverse along the stationary phase, a high surface area material can minimize a total volume of the stationary phase. High surface areas can be achieved with porous materials. In the previously described hydrosol formation process, porous silica can be formed by the addition of a polymer to the initial pre-hydrosol mixture. The polymer also forms a continuous network and the polymer network is interconnected or interspersed with the network of the hydrosol and eventually the hydrogel. The polymer can either be added as a separate entity or can be generated during the hydrolysis reaction. Preferably, the polymer is a low molecular weight polymer having an average molecule weight of between about 1,000 g/mol and about 50,000 g/mol, more preferably between about 1,000 g/mol and about 30,000 g/mol, more preferably between about 5,000 g/mol and about 20,000 g/mol. The polymer can be present preferably in an amount of between about 0.05 g/mL and about 0.5 g/mL, more preferably between about 0.075 g/mL and about 0.3 g/mL. The polymer preferably has desirable characteristics of non-toxicity, hydrophilicity and solubility in the solution and can be either ionic or nonionic. In one embodiment, the polymer is an anionic polymer such as poly(sodium styrenesulfonate) or poly(potassium styrenesulfonate). In another embodiment, the polymer can be a nonionic polymer such as polyethylene glycol. The polymer can be removed or eluted prior to chromatography by rinsing with an appropriate solvent, such as water and/or alcohol. The column may be further prepared by methods such as supercritical drying or by the use of a reagent to coat the gel with hydrophobic groups (e.g. methyl groups) to maintain hydrolytic stability. The monolith can also be stored with the polymer network interspersed within.

The method also involves introducing the hydrosol into a capillary. The hydrosol is a stable phase and can have fluidity of a solution or a viscous solution. "Stable phase" is defined as an ability of the hydrosol to maintain a fluid state for a desired period of time, such as the time required to introduce the hydrosol into the capillary. Due to the small dimensions of the capillary, introducing the hydrosol into the capillary may be aided by the application of a modest vacuum.

The method also involves inducing gellation of the hydrosol to form the hydrogel. In one embodiment, the hydrogel is a monolith i.e. a solid comprising a continuous network of chemical bonds. Gellation can be induced in a number of ways known in the art. In one embodiment, gellation is induced by warming an aqueous mixture comprising alkoxysilanes and a catalyst. In another embodiment, gellation can be induced by warning the hydrosol. Gellation can be induced at temperatures between about 0° C. and 70° C. In another embodiment, the solution can be warmed to temperatures of between about 20° C. and about 70° C., preferably between about 30° C. and about 60° C., and more preferably between about 30° C. and about 50° C. In another embodiment, gellation can be induced by allowing the mixture to stand at a temperature of between about 20° C. and about 30° C. It is understood that the optimal temperature is dependent on reactant concentration, pH etc.

Figure 1B:
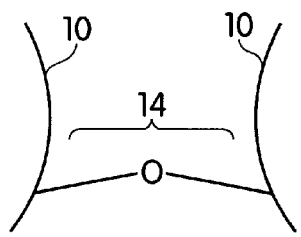
FIG. 1B is a schematic illustration of a product of a hydrolysis reaction between the two hydroxide groups shown in FIG. 1A.
Figure 2:
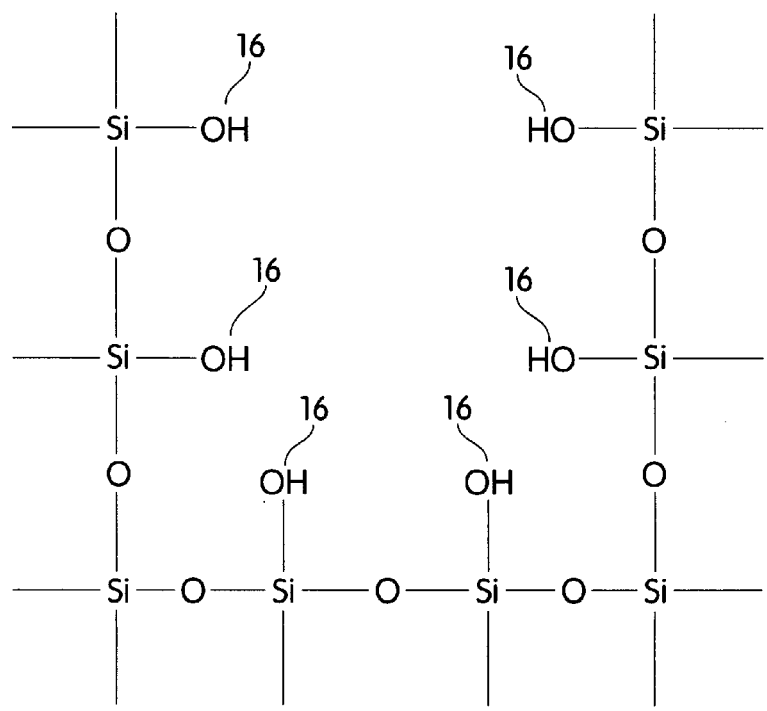
FIG. 2 is a molecular representation of a portion of silica having hydrolyzable hydroxide groups.

A particularly advantageous feature of the invention involves the formation of a monolith product where the hydrosol to gel transformation occurs with essentially no syneresis. "Syneresis" is the shrinkage in volume as a hydrosol progresses to a hydrogel. During both hydrosol and hydrogel formation, bonds are formed to generate a larger network without any decrease in volume. Bond formation can include hydrogen bonding or condensation reactions as discussed previously. As the gellation process continues and the network increases in volume, there reaches a point when bond formation results in a shrinkage of the network i.e. bond formation between two atoms causes several atoms to shift positions spatially such that the shifted atoms encompass a smaller local area or local volume. For example, FIG. 1A is a schematic illustration of two surfaces 10 each having a hydrolyzable hydroxide group 12. FIG. 1B schematically depicts the product of hydrolysis reaction between the two hydroxide groups to forms linkage 14, resulting in the two surfaces 10 being forced into closer proximity to each other. Thus, atoms at or near surface 10 shift in response to formation of linkage 14. The result may be a smaller local volume, as depicted schematically in FIG. 1B. In another example, a molecular representation of a surface of silica is shown in FIG. 2, the surface having hydrolyzable hydroxide groups 16. A hydrolysis reaction between any two groups 16 can cause at least a decrease in local volume and a resulting decrease in a total volume of the silica. Syneresis can be irreversible, the reversibility dependent on the ease of bond breaking.

Another embodiment of the present invention involves the formation of a capillary column having a monolith stationary phase. Conventional capillary columns comprise a cylindrical article having an inner wall and an outer wall and involve a stationary phase permanently positioned within a circular cross-section tube having inner diameters ranging from 5 µm to 0.5 mm. The cross section of the tube can have various closed shapes corresponding to the cross sectional areas of the circular tube. The tube wall is preferably glass but can be made of metal, plastic and other materials. Typically, the stationary phase comprises particles that are permanently packed adjacent the inner wall by various high pressure processes well known to those of ordinary skill in the art. The present invention of a monolith capillary column features an advantage over conventional capillary column due to facile preparation precluding the high pressure conditions. In particular, facile conditions are desired for smaller diameter capillaries (e.g. less than 100 µm diameter) where particle packing presents added difficulties due to the small dimensions.

Figure 3A:
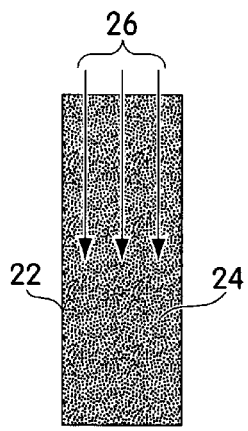
FIG. 3A is a schematic illustration of a cross-sectional slice of a capillary column containing a monolith support in which the monolith has undergone essentially no syneresis.
Figure 3B:
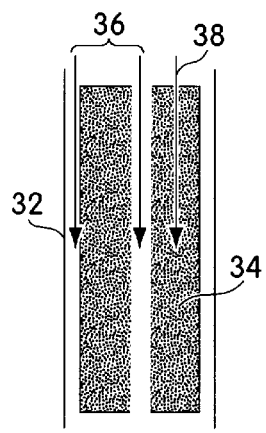
FIG. 3B is a schematic illustration of a cross-sectional slice of a capillary column containing a monolith support in which the monolith has undergone syneresis.

The ability to prepare a monolith without syneresis is an important feature in preparing monolith capillary columns. FIG. 3A shows a schematic example of a cross-sectional slice of an ideal capillary column 20 including capillary walls 22 and a monolith 24. During chromatography, arrows 26 show a pathway traversed by the mobile phase, the pathway maximizing contact between the mobile and stationary phases. FIG. 3B shows a schematic example of a cross-sectional slice of a capillary column 30 after syneresis, the column having a capillary wall 32 and a shrunken monolith 34. Due to a shrinkage in volume, channels can be formed between the monolith 34 and wall 32 or within the monolith. During chromatography, a flow path of least resistance exists within these gaps. A mobile phase traversing along this column may tend to follow the pathway indicated by arrows 36 instead of desired pathway 38. When the mobile phase follows pathways 36, portions of the stationary phase can be bypassed. Streaking of components to be separated can occur along the sides of the monolith and optimal separation of components may not be achieved. Due to factors such as temperature, hydrosol composition or even the application of an electric field, syneresis can occur to the extent that a volume of a material can decrease by a factor of 100.

Thus, another embodiment of the invention provides a capillary column having a monolith that is essentially free of syneresis. In one embodiment, the hydrosol is introduced into the capillary column, the hydrosol having a first volume. The first volume can be the volume of the hydrosol as defined by boundaries of the capillary. Gellation of the hydrosol can then be induced to form the monolith, the monolith having a second volume defined as the entire volume encompassed by the outer boundaries of the monolith. The second volume is at least about 95% of the first volume. Preferably, the second volume is at least about 99% of the first volume.

For silica monoliths, it has been discovered that producing a hydrosol having a relatively low ratio of $SiO_2$ units to solution volume results in a solid silica material that has undergone essentially no syneresis, as discussed in Jones et al. J. Non-Crystalline Solids, Vol. 101, pp. 123–126 (1988). In one embodiment, the hydrosol has an $SiO_2$ concentration of less than about 5 g/mL, preferably between about 3 g/mL and about 5 g/mL and more preferably between about 4 g/mL and about 5 g/mL. A balance should be achieved between preventing syneresis and reducing the structural integrity of the silica material which can be caused by an extremely low $SiO_2$ concentration. A further decrease in $SiO_2$ concentration may reduce a number of silicon backbone units and a brittle silica product may result.

In another embodiment, gellation is induced inside a capillary to provide a capillary column comprising a monolith. An advantageous feature of inducing gellation inside a capillary is the possibility of a covalent attachment between a capillary inner wall and the monolith, providing the column with a structural integrity that maintains the monolith within the column. A covalent attachment refers to the formation of a covalent chemical bond between the monolith and the capillary. For example, the capillary can be made of glass. A surface of the glass, preferably the inner wall of the glass capillary, can have condensible chemical groups. In one embodiment, the groups can be terminal Si—OH groups which can undergo a condensation reaction with the monolith which also has condensible chemical groups. For example, the monolith can have terminal M—OH groups which can react with Si—OH groups of the inner capillary wall to produce a covalent M—O—Si linkage between the monolith and the capillary. In one embodiment, M of the monolith can be any metal or main group element, such as silicon to provide an Si—O—Si linkage.

To allow the mobile phase to pass through the monolith, preferably the monolith is a porous monolith having pores of an average pore dimension or diameter. Preferably the average pore dimension is between about 0.1 $\mu$m and about 10 $\mu$m, and more preferably between about 0.25 $\mu$m and about 5 $\mu$m.

Figure 4A:
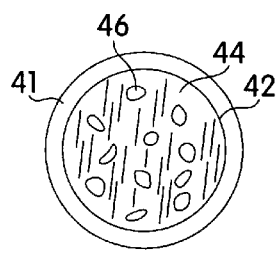
FIG. 4A is a schematic cross-sectional area of a capillary column containing a monolith support in which the monolith has undergone essentially no syneresis.

When there is a covalent attachment between the inner capillary wall and the monolith, the capillary column can have also have pores defined by a portion of the monolith, a portion of the wall and the covalent bonds. Such pores in a capillary column that undergoes essentially no syneresis have dimensions comparable to the pores of the monolith. FIG. 4A shows a schematic cross-sectional area of a capillary column having a monolith that is formed with essentially no syneresis. Capillary column 40 has a capillary 41 comprising an inner wall 42. Monolith 44 is attached to inner wall 42. Monolith 44 also has pores, for example the cross-section of pore 46, which have a first mean diameter.

Figure 4B:
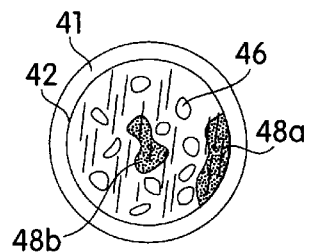
FIG. 4B is a schematic cross-sectional area of a capillary column containing a monolith support in which the monolith has undergone syneresis and featuring the different types of channels in the column.
Figure 5A:
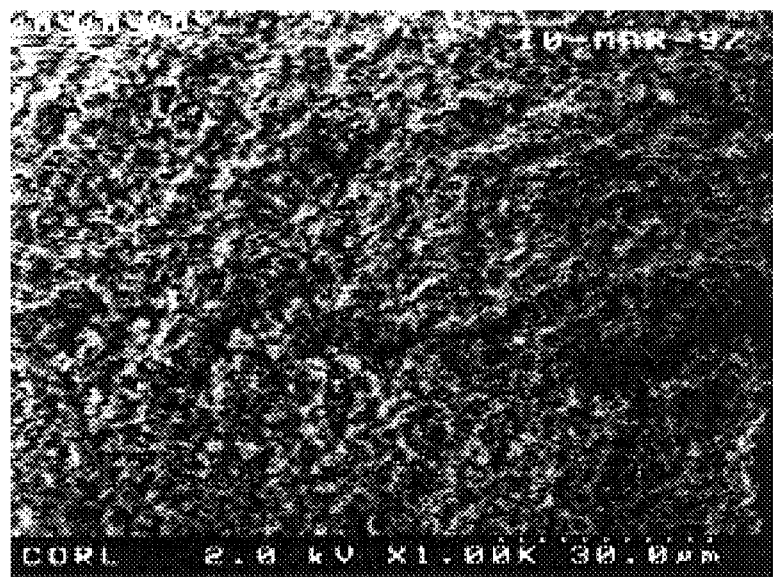
FIG. 5A is a photocopy of an electron micrograph of a silica monolith prepared as described in the example, and the scale represents a total distance of 30 $\mu$m.
Figure 5B:
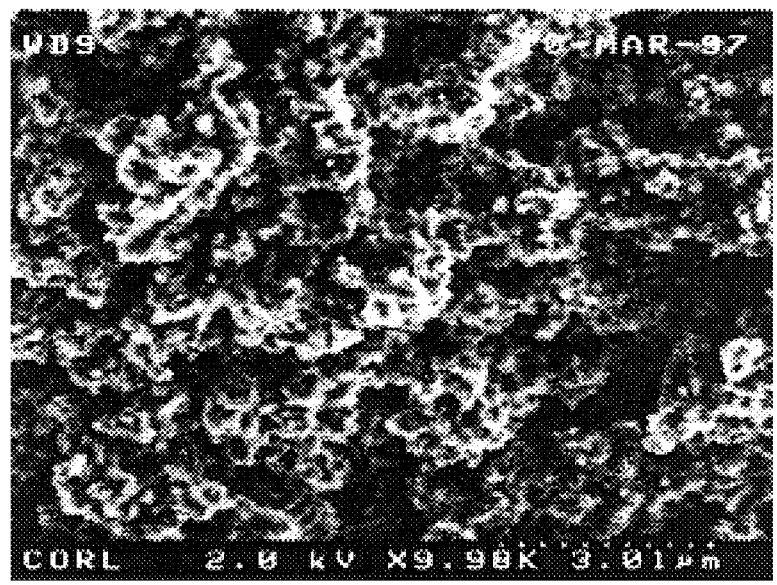
FIG. 5B is a photocopy of an expanded electron micrograph of FIG. 5A where the scale represents a total distance of 3 $\mu$m.

FIG. 4B schematically illustrates a cross-sectional area of a capillary column 50 having a monolith that is formed with syneresis. Syneresis causes a shrinkage in volume of the monolith resulting in deleterious effects such as the formation of channels. These channels can have excessively large dimensions that can provide, at least in part, a flow path of least resistance for portions of the mobile phase to bypass portions of the stationary phase. The extent of absorption/desorption of the mobile phase is minimized and streaking of the component bands can occur, resulting in poor resolution. In FIG. 4B, channels such as channel 48a can be formed when syneresis causes bonds between the monolith and the wall to break. In addition, channels may be formed within the monolith, such as channel 48b.

Another embodiment provides a capillary column having a silica monolith where channels have a second mean diameter, such that the second mean diameter is greater than the first mean diameter (of the pores) by less than about 150% of the first mean diameter, preferably about 125% of the first mean diameter, more preferably less than about 110% of the first mean diameter, more preferably less than about 105% of the first mean diameter, and even more preferably less than about 101% of the first mean diameter.

In another embodiment, the method allows further derivatization of the monolith. This derivatization allows tailoring of the monolith for a variety of chromatographic separations. For example, a surface can be incorporated into the monolith that is useful for reverse phase chromatography. Such surfaces can comprise long chain alkyls or other nonpolar groups. If, for example, the monolith is silica, the surface may include Si—OH or Si—OR groups that can be derivatized to form other Si—O-linkages to other organic groups, such as alkyls. Other derivatizations are known in the art and these are in accordance with the method of the invention.

Another aspect of the invention provides a capillary column having a monolith. The monolith can have features described above of a monolith prepared in accordance with the method of the present invention, including reaction conditions such as reactants and reactant concentration. In particular, the monolith of the capillary column is prepared with essentially no syneresis to avoid the formation of undesired channels that may result in poor chromatographic performance.

The function and advantage of these and other embodiments of the present invention will be more fully understood from the example below. The following example is intended to illustrate the benefits of the present invention, but do not exemplify the full scope of the invention.

Example: Preparation of a Silica Monolith Column

Tetramethylorthosilicate (980 $\mu$L) is combined with polyethylene glycol (1.5 g, wt. avg. MW=10,000 g/mol) and acetic acid (0.18 mL, 0.01 M) and the mixture is diluted with water to 10 mL. The mixture is then chilled to ~2° C. and shaken at 5 to 10 min. intervals over a period of about 30 min. The solution is then loaded into silica capillaries (typically 30 cm long, 300 $\mu$m o.d., 200 $\mu$m i.d.) by modest suction and sealed at both ends. The entire capillaries are subjected to a 40° C. bath for gellation and covalent wall attachment to occur. The capillaries are allowed to stand at room temperature for at least 10 h to the point that they can be used for chromatographic purposes or further processed.

A silica monolith column can also be prepared by following the above procedure but substituting 887 $\mu$L of tetraethylorthosilicate for the tetramethylorthosilicate.

Those skilled in the art would readily appreciate that all parameters listed herein are meant to be exemplary and that actual parameters will depend upon the specific application for which the methods and apparatus of the present invention are used. It is, therefore, to be understood that the foregoing embodiments are presented by way of example only and that, within the scope of the appended claims and equivalents thereto, the invention may be practiced otherwise than as specifically described.

What is claimed is:

1. A capillary column, comprising:
   a porous silica monolith having pores of a first mean diameter and channels of a second mean diameter, wherein the second mean diameter is greater than the first mean diameter by less than about 150% of the first mean diameter, wherein the column is free of deleterious effects due to syneresis.

2. A capillary column as in claim 1, wherein the second mean diameter is greater than the first mean diameter by less than about 125% of the first mean diameter.

3. A capillary column as in claim 1, wherein the second mean diameter is greater than the first mean diameter by less than about 110% of the first mean diameter.

4. A capillary column as in claim 1, wherein the second mean diameter is greater than the first mean diameter by less than about 105% of the first mean diameter.

5. A capillary column as in claim 1, wherein the second mean diameter is greater than the first mean diameter by less than about 101% of the first mean diameter.

* * * * *